(12) United States Patent
Ranpura

(10) Patent No.: US 8,311,610 B2
(45) Date of Patent: Nov. 13, 2012

(54) BIOPSY TISSUE MARKER

(75) Inventor: Himanshu M. Ranpura, Laveen, AZ (US)

(73) Assignee: C. R. Bard, Inc., Murray Hill, NJ (US)

(*) Notice: Subject to any disclaimer, the term of this patent is extended or adjusted under 35 U.S.C. 154(b) by 197 days.

(21) Appl. No.: 12/747,895

(22) PCT Filed: Jan. 22, 2009

(86) PCT No.: PCT/US2009/031688
§ 371 (c)(1),
(2), (4) Date: Jun. 11, 2010

(87) PCT Pub. No.: WO2009/099767
PCT Pub. Date: Aug. 13, 2009

(65) Prior Publication Data
US 2010/0331668 A1    Dec. 30, 2010

Related U.S. Application Data

(60) Provisional application No. 61/025,128, filed on Jan. 31, 2008.

(51) Int. Cl.
*A61B 19/00* (2006.01)
(52) U.S. Cl. .......... 600/414; 600/420; 600/424
(58) Field of Classification Search .......... 600/407–430; 424/423–426; 623/1, 11, 12
See application file for complete search history.

(56) References Cited

U.S. PATENT DOCUMENTS

| | | | |
|---|---|---|---|
| 2,192,270 A | 3/1940 | McGowan | |
| 2,481,408 A | 9/1949 | Fuller et al. | |
| 2,832,888 A | 4/1958 | Houston | |
| 2,899,362 A | 8/1959 | Sieger, Jr. et al. | |
| 2,907,327 A | 10/1959 | White | |
| 3,341,417 A | 9/1967 | Sinaiko | |
| 3,402,712 A | 9/1968 | Eisenhand | |
| 3,516,412 A | 6/1970 | Ackerman | |
| 3,593,343 A | 7/1971 | Viggers | |
| 3,757,781 A | 9/1973 | Smart | |
| 3,818,894 A | 6/1974 | Wichterle et al. | |
| 3,823,212 A | 7/1974 | Chvapil | |
| 3,921,632 A | 11/1975 | Bardani | |
| 4,005,699 A | 2/1977 | Bucalo | |
| 4,007,732 A | 2/1977 | Kvavle et al. | |
| 4,041,931 A | 8/1977 | Elliott et al. | |
| 4,103,690 A | 8/1978 | Harris | |

(Continued)

FOREIGN PATENT DOCUMENTS

DE    1029528 B    5/1958

(Continued)

OTHER PUBLICATIONS

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.

(Continued)

*Primary Examiner* — Sanjay Cattungal

(57) ABSTRACT

A biopsy site marker is disclosed. The biopsy site marker includes a first marker element and a second marker element. The first marker element is configured for detection by a first imaging modality. The second marker element is configured for detection by a second imaging modality different from the first imaging modality. The second marker element may be a non-absorbable wire having a predetermined shape and is substantially engaged with the first marker element.

68 Claims, 7 Drawing Sheets

U.S. PATENT DOCUMENTS

| | | |
|---|---|---|
| 4,105,030 A | 8/1978 | Kercso |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,028 A | 2/1991 | Leonard et al. |
| 5,012,818 A | 5/1991 | Joishy |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,613 A | 6/1994 | Houge et al. |
| 5,328,955 A | 7/1994 | Rhee et al. |
| 5,334,381 A | 8/1994 | Unger |
| 5,353,804 A | 10/1994 | Kornberg et al. |
| 5,354,623 A | 10/1994 | Hall |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,667,767 A | 9/1997 | Greff et al. |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,747,060 A | 5/1998 | Sackler et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,830,178 A | 11/1998 | Jones et al. |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |

| Patent No. | Kind | Date | Inventor |
|---|---|---|---|
| 5,902,310 | A | 5/1999 | Foerster et al. |
| 5,911,705 | A | 6/1999 | Howell |
| 5,916,164 | A | 6/1999 | Fitzpatrick et al. |
| 5,921,933 | A | 7/1999 | Sarkis et al. |
| 5,922,024 | A | 7/1999 | Janzen et al. |
| 5,928,626 | A | 7/1999 | Klaveness et al. |
| 5,928,773 | A | 7/1999 | Andersen |
| 5,941,439 | A | 8/1999 | Kammerer et al. |
| 5,941,890 | A | 8/1999 | Voegele et al. |
| 5,942,209 | A | 8/1999 | Leavitt et al. |
| 5,948,425 | A | 9/1999 | Janzen et al. |
| 5,954,670 | A | 9/1999 | Baker |
| 5,972,817 | A | 10/1999 | Haines et al. |
| 5,989,265 | A | 11/1999 | Bouquet De La Joliniere et al. |
| 6,015,541 | A | 1/2000 | Greff et al. |
| 6,030,333 | A | 2/2000 | Sioshansi et al. |
| 6,053,925 | A | 4/2000 | Barnhart |
| 6,056,700 | A | 5/2000 | Burney et al. |
| 6,066,122 | A | 5/2000 | Fisher |
| 6,066,325 | A | 5/2000 | Wallace et al. |
| 6,071,301 | A | 6/2000 | Cragg et al. |
| 6,071,310 | A | 6/2000 | Picha et al. |
| 6,071,496 | A | 6/2000 | Stein et al. |
| 6,096,065 | A | 8/2000 | Crowley |
| 6,096,070 | A | 8/2000 | Ragheb et al. |
| 6,106,473 | A | 8/2000 | Violante et al. |
| 6,117,108 | A | 9/2000 | Woehr et al. |
| 6,120,536 | A | 9/2000 | Ding et al. |
| 6,142,955 | A | 11/2000 | Farascioni et al. |
| 6,159,445 | A | 12/2000 | Klaveness et al. |
| 6,161,034 | A | 12/2000 | Burbank et al. |
| 6,162,192 | A | 12/2000 | Cragg et al. |
| 6,173,715 | B1 | 1/2001 | Sinanan et al. |
| 6,174,330 | B1 | 1/2001 | Stinson |
| 6,177,062 | B1 | 1/2001 | Stein et al. |
| 6,181,960 | B1 | 1/2001 | Jensen et al. |
| 6,183,497 | B1 | 2/2001 | Sing et al. |
| 6,190,350 | B1 | 2/2001 | Davis et al. |
| 6,200,258 | B1 | 3/2001 | Slater et al. |
| 6,203,524 | B1 | 3/2001 | Burney et al. |
| 6,203,568 | B1 | 3/2001 | Lombardi et al. |
| 6,213,957 | B1 | 4/2001 | Milliman et al. |
| 6,214,045 | B1 | 4/2001 | Corbitt, Jr. et al. |
| 6,214,315 | B1 | 4/2001 | Greff et al. |
| 6,220,248 | B1 | 4/2001 | Voegele et al. |
| 6,224,630 | B1 | 5/2001 | Bao et al. |
| 6,228,049 | B1 | 5/2001 | Schroeder et al. |
| 6,228,055 | B1 | 5/2001 | Foerster et al. |
| 6,231,615 | B1 | 5/2001 | Preissman |
| 6,234,177 | B1 | 5/2001 | Barsch |
| 6,241,687 | B1 | 6/2001 | Voegele et al. |
| 6,241,734 | B1 | 6/2001 | Scribner et al. |
| 6,251,418 | B1 | 6/2001 | Ahern et al. |
| 6,261,243 | B1 | 7/2001 | Burney et al. |
| 6,261,302 | B1 | 7/2001 | Voegele et al. |
| 6,264,917 | B1 | 7/2001 | Klaveness et al. |
| 6,270,464 | B1 | 8/2001 | Fulton, III et al. |
| 6,270,472 | B1 | 8/2001 | Antaki et al. |
| 6,287,278 | B1 | 9/2001 | Woehr et al. |
| 6,287,332 | B1 | 9/2001 | Bolz et al. |
| 6,289,229 | B1 | 9/2001 | Crowley |
| 6,312,429 | B1 | 11/2001 | Burbank et al. |
| 6,316,522 | B1 | 11/2001 | Loomis et al. |
| 6,335,029 | B1 | 1/2002 | Kamath et al. |
| 6,336,904 | B1 | 1/2002 | Nikolchev |
| 6,340,367 | B1 | 1/2002 | Stinson et al. |
| 6,343,227 | B1 | 1/2002 | Crowley |
| 6,347,240 | B1 | 2/2002 | Foley et al. |
| 6,347,241 | B2 | 2/2002 | Burbank et al. |
| 6,350,244 | B1 | 2/2002 | Fisher |
| 6,350,274 | B1 | 2/2002 | Li |
| 6,354,989 | B1 | 3/2002 | Nudeshima |
| 6,356,112 | B1 | 3/2002 | Tran et al. |
| 6,356,782 | B1 | 3/2002 | Sirimanne et al. |
| 6,358,217 | B1 | 3/2002 | Bourassa |
| 6,363,940 | B1 | 4/2002 | Krag |
| 6,371,904 | B1 | 4/2002 | Sirimanne et al. |
| 6,394,965 | B1 | 5/2002 | Klein |
| 6,403,758 | B1 | 6/2002 | Loomis |
| 6,405,733 | B1 | 6/2002 | Fogarty et al. |
| 6,409,742 | B1 | 6/2002 | Fulton, III et al. |
| 6,424,857 | B1 | 7/2002 | Henrichs et al. |
| 6,425,903 | B1 | 7/2002 | Voegele |
| 6,427,081 | B1 | 7/2002 | Burbank et al. |
| 6,450,937 | B1 | 9/2002 | Mercereau et al. |
| 6,450,938 | B1 | 9/2002 | Miller |
| 6,471,700 | B1 | 10/2002 | Burbank et al. |
| 6,478,790 | B2 | 11/2002 | Bardani |
| 6,506,156 | B1 | 1/2003 | Jones et al. |
| 6,511,468 | B1 | 1/2003 | Cragg et al. |
| 6,537,193 | B1 | 3/2003 | Lennox |
| 6,540,981 | B2 | 4/2003 | Klaveness et al. |
| 6,544,185 | B2 | 4/2003 | Montegrande |
| 6,551,253 | B2 | 4/2003 | Worm et al. |
| 6,554,760 | B2 | 4/2003 | Lamoureux et al. |
| 6,562,317 | B2 | 5/2003 | Greff et al. |
| 6,564,806 | B1 | 5/2003 | Fogarty et al. |
| 6,565,551 | B1 | 5/2003 | Jones et al. |
| 6,567,689 | B2 | 5/2003 | Burbank et al. |
| 6,575,888 | B2 | 6/2003 | Zamora et al. |
| 6,575,991 | B1 | 6/2003 | Chesbrough et al. |
| 6,605,047 | B2 | 8/2003 | Zarins et al. |
| 6,610,026 | B2 | 8/2003 | Cragg et al. |
| 6,613,002 | B1 | 9/2003 | Clark et al. |
| 6,616,630 | B1 | 9/2003 | Woehr et al. |
| 6,626,850 | B1 | 9/2003 | Chau et al. |
| 6,628,982 | B1 | 9/2003 | Thomas et al. |
| 6,636,758 | B2 | 10/2003 | Sanchez et al. |
| 6,638,234 | B2 | 10/2003 | Burbank et al. |
| 6,638,308 | B2 | 10/2003 | Corbitt, Jr. et al. |
| 6,652,442 | B2 | 11/2003 | Gatto |
| 6,656,192 | B2 | 12/2003 | Espositio et al. |
| 6,662,041 | B2 | 12/2003 | Burbank et al. |
| 6,699,205 | B2 | 3/2004 | Fulton, III et al. |
| 6,712,774 | B2 | 3/2004 | Voegele et al. |
| 6,712,836 | B1 | 3/2004 | Berg et al. |
| 6,716,444 | B1 | 4/2004 | Castro et al. |
| 6,725,083 | B1 | 4/2004 | Burbank et al. |
| 6,730,042 | B2 | 5/2004 | Fulton et al. |
| 6,730,044 | B2 | 5/2004 | Stephens et al. |
| 6,746,661 | B2 | 6/2004 | Kaplan |
| 6,746,773 | B2 | 6/2004 | Llanos et al. |
| 6,752,154 | B2 | 6/2004 | Fogarty et al. |
| 6,766,186 | B1 | 7/2004 | Hoyns et al. |
| 6,774,278 | B1 | 8/2004 | Ragheb et al. |
| 6,780,179 | B2 | 8/2004 | Lee et al. |
| 6,824,507 | B2 | 11/2004 | Miller |
| 6,824,527 | B2 | 11/2004 | Gollobin |
| 6,846,320 | B2 | 1/2005 | Ashby et al. |
| 6,862,470 | B2 | 3/2005 | Burbank et al. |
| 6,863,685 | B2 | 3/2005 | Davila et al. |
| 6,899,731 | B2 | 5/2005 | Li et al. |
| 6,918,927 | B2 | 7/2005 | Bates et al. |
| 6,936,014 | B2 | 8/2005 | Vetter et al. |
| 6,939,318 | B2 | 9/2005 | Stenzel |
| 6,945,973 | B2 | 9/2005 | Bray |
| 6,951,564 | B2 | 10/2005 | Espositio et al. |
| 6,992,233 | B2 | 1/2006 | Drake et al. |
| 6,993,375 | B2 | 1/2006 | Burbank et al. |
| 6,994,712 | B1 | 2/2006 | Fisher et al. |
| 6,996,433 | B2 | 2/2006 | Burbank et al. |
| 7,001,341 | B2 | 2/2006 | Gellman et al. |
| 7,008,382 | B2 | 3/2006 | Adams et al. |
| 7,014,610 | B2 | 3/2006 | Koulik |
| 7,025,765 | B2 | 4/2006 | Balbierz et al. |
| 7,044,957 | B2 | 5/2006 | Foerster et al. |
| 7,047,063 | B2 | 5/2006 | Burbank et al. |
| 7,083,576 | B2 | 8/2006 | Zarins et al. |
| 7,125,397 | B2 | 10/2006 | Woehr et al. |
| 7,172,549 | B2 | 2/2007 | Slater et al. |
| 7,214,211 | B2 | 5/2007 | Woehr et al. |
| 7,229,417 | B2 | 6/2007 | Foerster et al. |
| 7,236,816 | B2 | 6/2007 | Kumar et al. |
| 7,264,613 | B2 | 9/2007 | Woehr et al. |
| 7,294,118 | B2 | 11/2007 | Saulenas et al. |
| 7,297,725 | B2 | 11/2007 | Winterton et al. |
| 7,329,402 | B2 | 2/2008 | Unger et al. |
| 7,416,533 | B2 | 8/2008 | Gellman et al. |

| | | |
|---|---|---|
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,569,065 B2 | 8/2009 | Chesbrough et al. |
| 7,577,473 B2 | 8/2009 | Davis et al. |
| 7,637,948 B2 | 12/2009 | Corbitt, Jr. |
| 7,651,505 B2 | 1/2010 | Lubock et al. |
| 7,877,133 B2 | 1/2011 | Burbank et al. |
| 2001/0006616 A1 | 7/2001 | Leavitt et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0193815 A1 | 12/2002 | Foerster et al. |
| 2002/0193867 A1 | 12/2002 | Gladdish, Jr. et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236212 A1 | 11/2004 | Jones et al. |
| 2004/0236213 A1 | 11/2004 | Jones et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0116573 A1 | 6/2006 | Field et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2006/0292690 A1 | 12/2006 | Liu et al. |
| 2007/0021642 A1 | 1/2007 | Lamoureux et al. |
| 2007/0038145 A1 | 2/2007 | Field |
| 2007/0057794 A1 | 3/2007 | Gisselberg et al. |
| 2007/0083132 A1 | 4/2007 | Sharrow |
| 2007/0087026 A1 | 4/2007 | Field |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0033280 A1 | 2/2008 | Lubock et al. |
| 2008/0039819 A1 | 2/2008 | Jones et al. |
| 2008/0097199 A1 | 4/2008 | Mullen |
| 2008/0188768 A1 | 8/2008 | Zarins et al. |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0030309 A1 | 1/2009 | Jones et al. |
| 2009/0069713 A1 | 3/2009 | Adams et al. |
| 2009/0076484 A1 | 3/2009 | Fukaya |
| 2009/0093714 A1 | 4/2009 | Chesbrough et al. |
| 2009/0131825 A1 | 5/2009 | Burbank et al. |
| 2009/0171198 A1 | 7/2009 | Jones et al. |
| 2009/0216118 A1 | 8/2009 | Jones et al. |
| 2010/0010341 A1 | 1/2010 | Talpade et al. |
| 2010/0030072 A1 | 2/2010 | Casanova et al. |
| 2010/0030149 A1 | 2/2010 | Carr, Jr. |
| 2010/0082102 A1 | 4/2010 | Govil et al. |
| 2010/0204570 A1 | 8/2010 | Lubock |
| 2011/0028836 A1 | 2/2011 | Ranpura |

FOREIGN PATENT DOCUMENTS

| | | |
|---|---|---|
| EP | 0146699 A1 | 7/1985 |
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| GB | 708148 | 4/1954 |

| | | | |
|---|---|---|---|
| JP | 2131757 A | 5/1990 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9806346 A1 | 2/1998 |
| WO | 9908607 A1 | 2/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Fucci, V., et al., "Large Bowel Transit Times Using Radioopaque Markers in Normal Cats", J. of Am. Animal Hospital Assn., Nov.-Dec. 31, 1995 (6) 473-477.

Schindlbeck, N.E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large-Tissue Engineering", Biotechnol. Prog., vol. 14, No. 1, pp. 134-140, 1998.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

Press release for Biopsys Ethicon Endo-Surgery (Europe) GmbH; The Mammotome Vacuum Biopsy System. From: http://www.medicine-news.com/articles/devices/mammotome.html. 3 pages.

Johnson & Johnson: Breast Biopsy (minimally invasive): Surgical Technique: Steps in the MAMOTOME Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

BIOPSY TISSUE MARKER

CROSS REFERENCE TO RELATED APPLICATIONS

This application is a U.S. national phase of International Application No. PCT/US2009/031688, filed Jan. 22, 2009, based upon U.S. Provisional Patent Application Ser. No. 61/025,128, filed Jan. 31, 2008, from which priority is claimed.

FIELD OF THE INVENTION

The present invention relates generally to surgical devices, and more specifically, to biopsy tissue markers.

BACKGROUND

In modern medical practice small tissue samples, known as biopsy specimens, are often removed from tumors, lesions, organs, muscles and other tissues of the body. The removal of tissue samples may be accomplished by open surgical technique, or through the use of a specialized biopsy instrument such as a biopsy needle, including vacuum assisted biopsy devices.

After a tissue sample has been removed, it is typically subjected to diagnostic tests or examinations to determine cytology, histology, presence or absence of chemical substances that act as indicators for disease states, or the presence of bacteria or other microbes. The above mentioned and other diagnostic tests and examinations per se are well known in the art and need not be described here. As is known, obtaining a tissue sample by biopsy and the subsequent examination are frequently employed in the diagnosis of cancers and other malignant tumors or to confirm that a suspected lesion or tumor is not malignant, and are frequently used to devise a plan for the appropriate surgical procedure or other course of treatment.

Examination of tissue samples taken by biopsy is of particular significance in the diagnosis and treatment of breast cancer, the most common cancer suffered by women throughout the world. Proper diagnostic procedures, frequent examination by well known techniques such as "mammography" and prompt subsequent surgical treatment have, however, significantly reduced the mortality rate caused by this form of cancer. For this reason, references in the background and description of embodiments are made to marking biopsy sites in human and other mammalian breasts, although the invention is suitable for marking biopsy sites in other parts of the human and other mammalian body as well.

Thus, as is known, when an abnormal mass in the breast is found by physical examination or mammography, a biopsy procedure follows. A biopsy procedure can include an open surgical biopsy or a technique such as Fine Needle Aspiration Biopsy (FNAB) or less invasive stereotactic needle biopsy.

Oftentimes, in connection with biopsy procedures, the radiologist or surgeon feels a marker should be used to mark the site of the biopsy for later reference. Such markers can be formed of surgical alloys such as titanium alloys, including shape memory alloys. It is generally important that the marker be capable of being imaged by an imaging modality, such as magnetic resonance imaging (MRI), ultrasound, and/or X-ray. Placement of a marker can be an important step to take since most abnormalities biopsied are small or subtle and can become extremely difficult or impossible to identify after a core biopsy procedure. When a biopsy result is abnormal and an excision or lumpectomy is necessary, the marker allows accurate localization of the abnormal site for removal so that as little tissue as necessary is removed while optimizing the chance of clear margins.

Most patients have normal (benign) results from these types of biopsy, however, the presence of the marker is helpful when seen on follow-up mammograms; it shows exactly where the area was biopsied. This avoids confusion in interpretation of follow-up mammograms and can prevent the need for future biopsies in that same area.

Despite successful use of various marker structures, a need in the art continues to exist for biopsy site markers that resist migration from the deployed location, such as the biopsy cavity created as a result of the biopsy procedure, even when the breast tissue is moved, manipulated or decompressed. Moreover, such desired markers should remain detectable at the biopsy site by one of the above-mentioned modalities.

SUMMARY OF THE INVENTION

A biopsy site marker is disclosed. The biopsy site marker includes a first marker element and a second marker element. The first marker element is detectable by a first imaging modality and is a non-absorbable cylinder. The second marker element is detectable by a second imaging modality and is not detectable by the first imaging modality. The second marker element is a non-absorbable wire having a helical shape and is substantially engaged with the first marker element.

In another embodiment, a biopsy site marker is disclosed. The biopsy site marker includes a first marker element and a second marker element. The first marker element is detectable by a first imaging modality and is a non-absorbable cylinder containing at least one hole. The second marker element is detectable by a second imaging modality and is not detectable by the first imaging modality. The second marker element is a non-absorbable peg substantially engaged with the hole of the first marker element.

In yet another embodiment, a biopsy site marker is disclosed. The biopsy site marker includes a first marker element and a second marker element. The first marker element is a non-absorbable material detectable by a first imaging modality. The second marker element is detectable by a second imaging modality and is not detectable by the first imaging modality. The second marker element is a non-absorbable material substantially engaged with the first marker element. The second marker has a shape including a mesh shape, a pyramid shape, a cube shape, a sphere shape, a rectangular shape, or a square shape.

In another embodiment, a method for imaging a subcutaneous biopsy cavity is disclosed and includes placing a marker element into the biopsy cavity. The marker element includes a first marker element and a second marker element. The first marker element is a non-absorbable cylinder. The second marker element is a non-absorbable wire having a helical shape and is substantially engaged with the first marker element. The method further includes detecting the first marker element using a first imaging modality and detecting the second marker element using a second imaging modality.

In still another embodiment, a method for imaging a subcutaneous biopsy cavity is disclosed and includes placing a marker element into the biopsy cavity. The marker element includes a first marker element and a second marker element. The first marker element includes a non-absorbable cylinder containing at least one hole. The second marker element is a non-absorbable peg substantially engaged with the hole of the first marker element. The method further includes detecting the first marker element using a first imaging modality and detecting the second marker element using a second imaging modality.

In yet another embodiment, a method for imaging a subcutaneous biopsy cavity is disclosed and includes placing a marker element into the biopsy cavity. The marker element includes a first marker element and a second marker element. The first marker element includes a non-absorbable material. The second marker element is a non-absorbable material substantially engaged with the first marker element. The second marker element has a shape including a mesh shape, a pyramid shape, a cube shape, a sphere shape, a rectangular shape, or a square shape. The method further includes detecting the first marker element using a first imaging modality and detecting the second marker element using a second imaging modality.

DETAILED DESCRIPTION OF THE INVENTION

Referring to FIGS. 1, 2, 3, 4, 5, 6, 7, 8, 9, and 10, a biopsy site marker is shown and is generally designated 100. The biopsy site marker 100 includes a first marker element 102 having a cylindrical shape or contour. The cylindrical shape or contour can fill the void of the biopsy cavity after the tissue sample is removed during the biopsy process.

Figure 1:
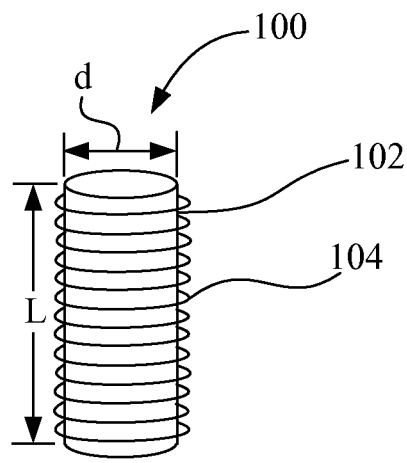
FIGS. 1-10 are illustrations depicting a first embodiment of a biopsy site marker.

In more particularity, and as seen in FIG. 1, a cylindrical shape or contour is generally defined by a discrete segment of a body having a diameter (d) and a length (L). The cylindrical shape has a cross-section that is curved. In an embodiment, the length is greater than the diameter. In an embodiment, and as seen in FIG. 1, the length of the cylindrical shape may be straight. In another embodiment, the length of cylindrical shape may be curved. In an embodiment, the cylindrical shape is generally solid. The biopsy site marker 100 may be made of a polymer, metal, or ceramic material and is generally proportioned to enable imaging of the marker by a chosen modality, and proportioned to allow fitment of the marker in a deployment device of desired gauge size, for instance, 17 or 20.

The biopsy site marker 100 further includes a second marker element 104 that is a non-absorbable, biocompatible wire. The second marker element 104 has a helical shape and is substantially engaged with the first marker element 102. In certain embodiments, the turns of the helix have a generally uniform shape, having coil-to-coil diameter variation generally not exceeding 20% of the average coil diameter. The loops or coils may extend along the majority of the length of the wire, typically at least 50%, such as at least about 70%, of even greater than about 80% of its length. "Substantially engaged" as used herein refers to materials that are engaged to prevent the at least two marker elements from disengaging.

In an exemplary embodiment, the second marker element 104 can be imaged by a second imaging modality that is different than the first imaging modality. For instance, the material of the first marker element 102 is different than the material of the second marker element 104 so the first marker element 102 and second marker element 104 are imaged by two different imaging modalities.

In a particular embodiment, the biopsy site marker 100 can be made from one or more extended use approved medical materials that can be medically imaged. Medical imaging means include, for example, radiographic imaging modalities, magnetic resonance imaging (MRI), ultrasonography, fluoroscopy, or computed tomography. For example, the materials can be any non-absorbable, biocompatible materials. A "non-absorbable, biocompatible material" as used herein refers to a material that does not cause any adverse reactions to a patient's health and that does not disintegrate over the lifetime of the patient. Non-absorbable, biocompatible materials include metal containing materials, polymer materials, ceramic materials, or composite materials that include metals, polymers, or combinations of metals and polymers.

The polymer materials can include polyvinyl alcohol, polyurethanes, polyolefins, polyesters, polypropylenes, polyimides, polyetherimides, fluoropolymers, thermoplastic liquid polymers (LCP) such as, for example, Vectra® by Celanese, polyethylether ketones such as, for example, PEEK™ by Vitrex, polyamides, polycarbonates such as, for example, Makrolon® by Bayer Polymers, polysulfones, polyethersufones, polyphenylsulfones such as, for example, Radel® by Rowland Technologies, nylon, and nylon copolymers. In an embodiment, the first marker element 102 is a polymer material.

In a particular embodiment, the metal containing materials can be metals. Further, the metal containing materials can be ceramics. Also, the metals can be pure metals or metal alloys. The metals can include gold, iridium, nickel, rhodium, silver, tantalum, titanium, stainless steel and alloys thereof.

In an embodiment, the biopsy site marker 100 can be made of a shape-memory material. Exemplary shape-memory materials include nitinol, titanium, or any shape-memory polymers. In an exemplary embodiment, the second marker element 104 is a shape-memory material.

Figure 2:
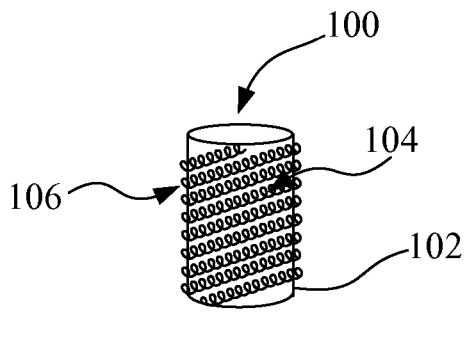

To enhance detection by an imaging modality, and as seen in FIG. 2, the second marker element 104 may have a twisted configuration. It should be noted that description of the twisted configuration refers to the texture of the wire, and not the overall shape, such as the cylindrical shape noted above. As used herein, the term 'twisted' and 'twisted configuration' generally denote a wire that is twisted to thereby form a plurality of loops 106 or coils along the helical shape of the second marker element 104. The loops or coils may extend along the majority of its length, typically at least 80% of its length. In certain embodiments, the coils have generally uniform shape, having coil-to-coil diameter variation generally not exceeding 20% of the average coil diameter. It is generally understood that the coils of the twisted configuration have a smaller diameter than the coils of the helical shape.

Figure 3:
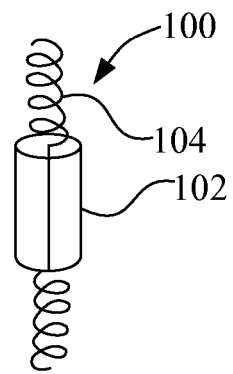
Figure 4:
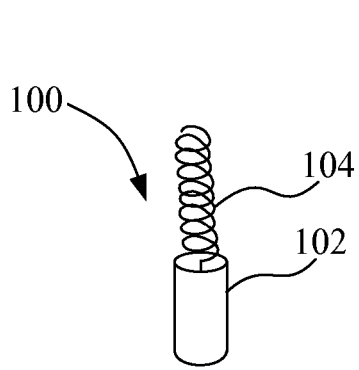

As seen in FIGS. 3 and 4, the first marker element 102 is cylindrical in shape and may be configured to engage the second marker element 104 to allow for the second marker element 104 to pass through and accommodate the second marker element 104. The first marker element 102 may be generally proportioned to leave a majority of the second marker element 104 exposed, to enable imaging of the second marker element 104 by a chosen modality.

Figure 5:
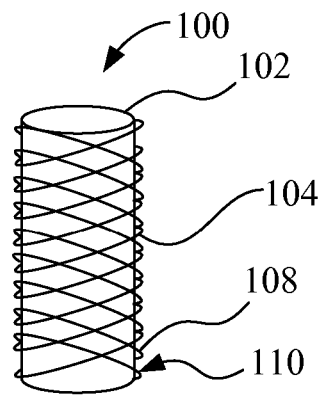
Figure 6:
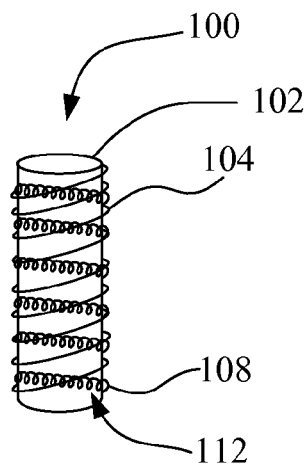
Figure 7:
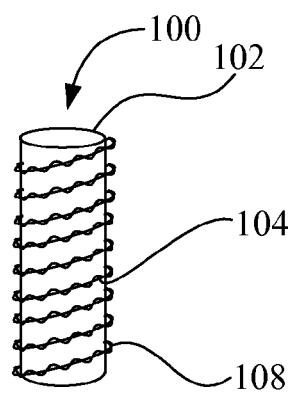

In an embodiment, and as seen in FIGS. 5, 6, 7, 8, 9, and 10, the biopsy site marker 100 may include a third marker element 108. The third marker element 108 is typically a non-absorbable, biocompatible material. The third marker element 108 can be in any suitable configuration such that it is substantially engaged with the first marker element 102, the second marker element 104, or a combination thereof. In an embodiment, and as seen in FIG. 5, the third marker element 108 can be a wire 110. Further, and as seen in FIG. 6, the third marker element 108 can have a twisted configuration having a plurality of loops 112. In another embodiment, and as seen in FIG. 7, the second marker element 104 of the biopsy site marker 100 can be braided with the third marker element 108.

Figure 8:
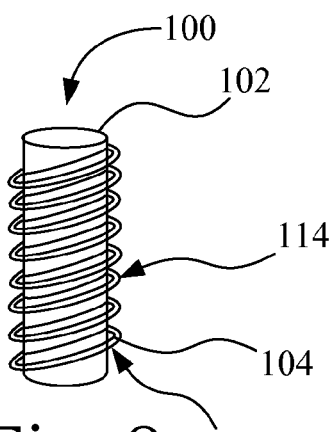
Figure 9:
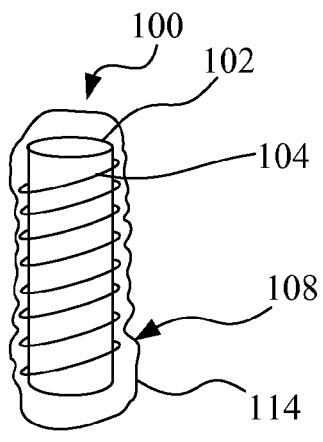
Figure 10:
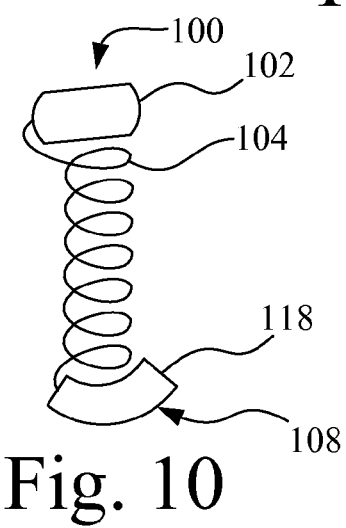

As seen in FIGS. 8 and 9, the third marker element 108 is a polymeric coating 114. In an embodiment, the polymeric coating 114 on the second marker element 104 increases the echogenity of the second marker element 104. Any polymer material that increases the echogenity of the second marker element 104 is envisioned. The polymeric coating 114 generally covers a majority of the outer surface of the second marker element 104, such as not less than 80% of the outer surface of the wire. In certain embodiments, the ends of the wire can be exposed (uncoated) and in other embodiments, such as that shown in FIG. 8, the entirety of the wire can be encapsulated with the polymeric coating 114. As seen in FIG. 9, the third marker element 108 is a polymeric coating 114 that encapsulates the entirety of the first marker element 102 and the second marker element 104. As seen in FIG. 10, the third marker element 108 is a cylinder 118 where the length is curved.

In an embodiment, the third marker element 108 can be imaged by a modality that is different than the imaging modality of the first marker element 102 and different than the imaging modality of the second marker element 104 of the biopsy site marker 100. For instance, the material of the third marker element 108 is different than the material of the first marker element 102 and the second marker element 104 so the first marker element 102, second marker element 104, and third marker element 108 can be imaged by three different imaging modalities. For instance, the first marker element 102 is a polymer, the second marker element 104 is a shape-memory material, and the third marker element 108 is another polymer. As stated earlier, imaging modalities include radiographic imaging modalities, magnetic resonance imaging (MRI), ultrasonography, fluoroscopy, or computed tomography.

In a further embodiment, the biopsy site marker 100 may further include a bioabsorbable cover. In an embodiment, the bioabsorbable cover is any suitable material used to encapsulate a medical implant that biodegrades within the biopsy cavity without any adverse reactions to the patient. Bioabsorbable materials include, for example, aliphatic polyesters such as homopolymers and copolymers of lactic acid, glycolic acid, lactide, glycolide, para-dioxanone, trimethylene carbonate, ε-caprolactone, polyorthoesters, polyethylene oxide, and blends thereof.

Figure 11:
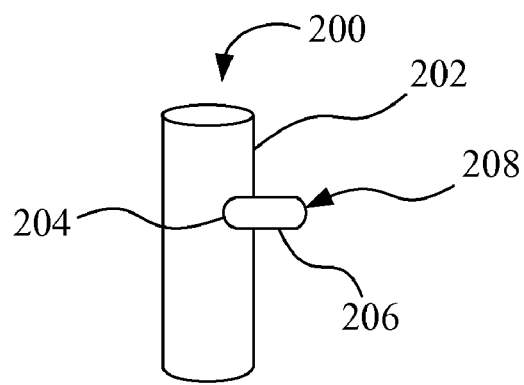
FIGS. 11-13 are illustrations depicting a second embodiment of a biopsy site marker.
Figure 12:
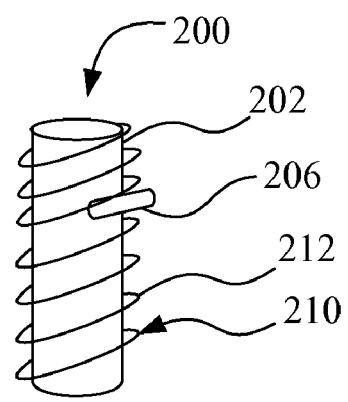
Figure 13:
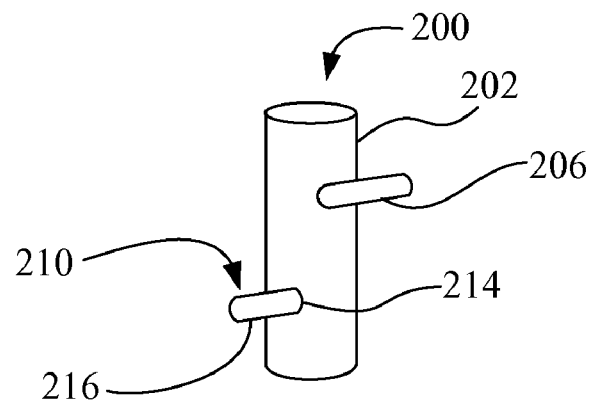

In accordance with another embodiment of the invention, referring to FIGS. 11, 12, and 13, a biopsy site marker is shown and is generally designated 200. As seen in FIG. 11, the biopsy site marker 200 generally includes a first marker element 202 that is a non-absorbable, biocompatible material that can be imaged by a first imaging modality. The first marker element 202 has a cylindrical shape or contour. The cylindrical shape or contour can fill the void of the biopsy cavity after the tissue sample is removed during the biopsy process. The first marker element 202 contains at least one hole 204.

The biopsy site marker 200 further includes a second marker element 206 that is a non-absorbable, biocompatible peg 208. The second marker element 206 is substantially engaged with the hole 204 of the first marker element 202. "Substantially engaged" as used herein refers to materials that are engaged to prevent the first marker element 202 and the second marker element 206 from disengaging. In an exemplary embodiment, the first marker element 202 and the second marker element 206 are configured to fill a biopsy void. Further, the second marker element 206 can be imaged by a second imaging modality that is different than the first imaging modality. For instance, the material of the first marker element 202 is different than the material of the second marker element 206 so the first marker element 202 and second marker element 206 are imaged by two different imaging modalities.

In a particular embodiment, the biopsy site marker 200 can be made from one or more extended use approved medical materials that can be medically imaged. Medical imaging modalities include, for example, radiographic imaging modalities, magnetic resonance imaging (MRI), ultrasonography, fluoroscopy, or computed tomography.

For example, the materials can be any non-absorbable, biocompatible materials. A "non-absorbable, biocompatible material" as used herein refers to a material that does not cause any adverse reactions to a patient's health and that does not disintegrate over the lifetime of the patient. Non-absorbable, biocompatible materials include metal containing materials, polymer materials, or composite materials that include metals, polymers, or combinations of metals and polymers.

The polymer materials can include polyvinyl alcohol, polyurethane, polyolefin, polyester, polypropylene, or fluoropolymer. In an exemplary embodiment, the first marker element 202 is a polymer material.

In a particular embodiment, the metal containing materials can be metals. Further, the metal containing materials can be ceramics. Also, the metals can be pure metals or metal alloys. The metals can include gold, iridium, nickel, rhodium, silver, tantalum, titanium, stainless steel and alloys thereof. In an exemplary embodiment, the second marker element 206 is a metal.

In an embodiment, the biopsy site marker 200 can be made of a shape-memory material. Exemplary shape-memory materials include nitinol, titanium, or any shape-memory polymers.

In an embodiment, the biopsy site marker 200 may include a third marker element 210. The third marker element 210 is typically a non-absorbable, biocompatible material. In a further embodiment, the third marker element 210 can be substantially engaged with the first marker element 202, the second marker element 206, or a combination thereof. "Substantially engaged" as used herein refers to materials that are engaged to prevent the first marker element 202, second marker element 206, and the third marker element 210 from disengaging. For instance, the third marker element 210 can be in any suitable configuration and shape such that it is substantially engaged with the first marker element 202, the second marker element 206, or combination thereof. As seen in FIG. 12, the third marker element 210 can be a wire 212 having a helical shape. In an embodiment, the third marker element 210 can have a twisted configuration having a plurality of loops. As seen in FIG. 13, first marker element 202 may include a second hole 214 and the third marker element 210 may be a non-absorbable peg 216 substantially engaged with the second hole 214. In an embodiment, the third marker element 210 is a polymer coating.

In an embodiment, the third marker element 210 can be imaged by a modality that is different than the imaging modality of the first marker element 202 and different than the imaging modality of the second marker element 206 of the biopsy site marker 200. For instance, the material of the third marker element 210 is different than the material of the first marker element 202 and the second marker element 206 so the first marker element 202, second marker element 206, and third marker element 210 can be imaged by three different imaging modalities. For instance, the first marker element 202 is a polymer, the second marker element 206 is a metal, and the third marker element 210 is another polymer. As stated earlier, imaging modalities include radiographic imaging modalities, magnetic resonance imaging (MRI), ultrasonography, fluoroscopy, or computed tomography.

In a further embodiment, the biopsy site marker 200 may further include a bioabsorbable cover. In an embodiment, the bioabsorbable cover is any suitable material used to encapsulate a medical implant that biodegrades within the biopsy cavity without any adverse reactions to the patient. Bioabsorbable materials include, for example, aliphatic polyesters such as homopolymers and copolymers of lactic acid, glycolic acid, lactide, glycolide, para-dioxanone, trimethylene carbonate, ε-caprolactone, polyorthoesters, polyethylene oxide, and blends thereof.

In accordance with another embodiment of the invention, referring to FIGS. 14, 15, 16, 17, 18, 19, 20, and 21, a biopsy site marker is shown and is generally designated 300. The biopsy site marker 300 generally includes a first marker element 302 that is a non-absorbable, biocompatible material that can be imaged by a first imaging modality. The first marker element 302 can be in any suitable configuration that is envisioned. In an embodiment, the first marker element 302 is a cylinder 304. In another embodiment, the first marker element 302 is a wire. In another embodiment, the first marker element 302 is twisted wire.

Figure 14:
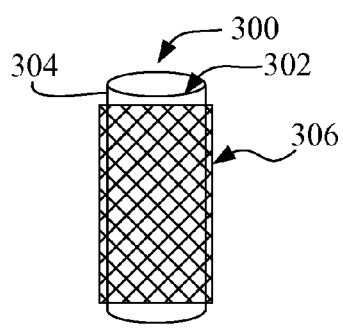
FIGS. 14-21 are illustrations depicting a third embodiment of a biopsy site marker.
Figure 15:
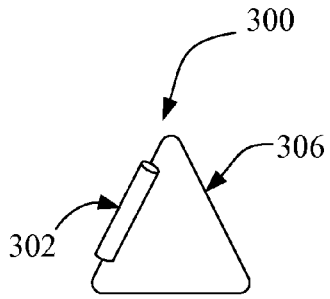
Figure 16:
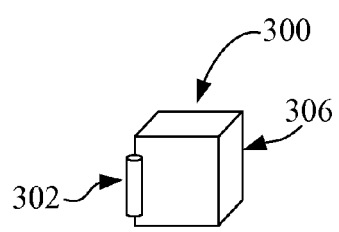
Figure 17:
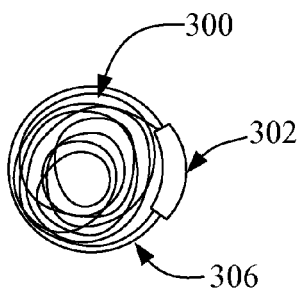
Figure 18:
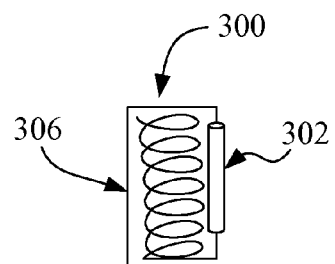
Figure 19:
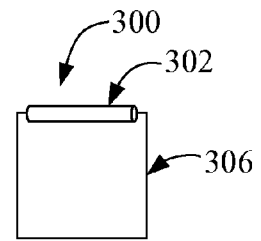

A second marker element 306 is substantially engaged with the first marker element. "Substantially engaged" as used herein refers to materials that are engaged to prevent the first marker element 302 and the second marker element 306 from disengaging. In an exemplary embodiment, the first marker element 302 and the second marker element 306 are configured to fill a biopsy void. The second marker element 306 may have any suitable shape that is echogenic and easily differentiated from tissue mass due to its geometric shape. In an embodiment, and as seen in FIG. 14, the second marker element 306 may have a mesh shape. In an embodiment, and as seen in FIG. 15, the second marker element 306 may have a pyramid shape. In an embodiment, and as seen in FIG. 16, the second marker element 306 may have a cube shape. In a further embodiment, and as seen in FIG. 17, the second marker element 306 may be wire-form having a sphere shape. In a further embodiment, and as seen in FIG. 18, the second marker element 306 may have a rectangular shape with at least a portion of the second marker element 306 having a helical shape. In a further embodiment, and as seen in FIG. 18, the second marker element 306 may have a square shape.

Although the second marker element 306 is illustrated as one wire, the second marker element 306 may be more than one wire of the same non-absorbable, biocompatible material. In an exemplary embodiment, the wire has a twisted configuration having a plurality of loops. The twisted configuration of the second marker element 306 increases the echogenity of the biopsy site marker 300.

In an exemplary embodiment, the second marker element 306 can be imaged by a second imaging modality that is different than the first imaging modality. For instance, the material of the first marker element 302 is different than the material of the second marker element 306, so the first marker element 302 and second marker element 306 are imaged by two different imaging modalities.

In a particular embodiment, the biopsy site marker 300 can be made from one or more extended use approved medical materials that can be medically imaged. Medical imaging modalities include, for example, radiographic imaging modalities, magnetic resonance imaging (MRI), ultrasonography, fluoroscopy, or computed tomography.

For example, the materials can be any non-absorbable, biocompatible materials. A "non-absorbable, biocompatible material" as used herein refers to a material that does not cause any adverse reactions to a patient's health and that does not disintegrate over the lifetime of the patient. Non-absorbable, biocompatible materials include metal containing materials, polymer materials, or composite materials that include metals, polymers, or combinations of metals and polymers.

The polymer materials can include polyvinyl alcohol, polyurethane, polyolefin, polyester, polypropylene, or fluoropolymer. In an embodiment, the first marker element 302 is a polymer material.

In a particular embodiment, the metal containing materials can be metals. Further, the metal containing materials can be ceramics. Also, the metals can be pure metals or metal alloys. The metals can include gold, iridium, nickel, rhodium, silver, tantalum, titanium, stainless steel and alloys thereof.

In an embodiment, the biopsy site marker 300 can be made of a shape-memory material. Exemplary shape-memory materials include nitinol, titanium, or any shape-memory polymers. In an embodiment, the second marker element 306 is a shape-memory material.

Figure 20:
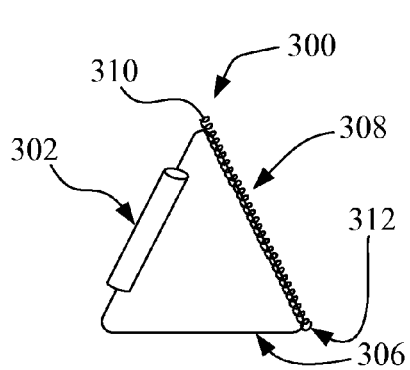
Figure 21:
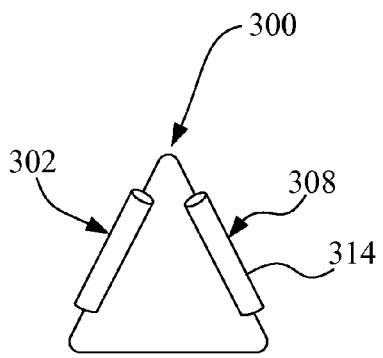

In an embodiment, and as seen in FIGS. 20 and 21, the biopsy site marker 300 may include a third marker element 308. The third marker element 308 is typically a non-absorbable, biocompatible material. In a further embodiment, the third marker element 308 can be substantially engaged with the first marker element 302, the second marker element 306, or combination thereof. The third marker element 308 can be in any suitable configuration such that it is substantially engaged with the first marker element 302, the second marker element 306, or combination thereof. In an embodiment, and as illustrated in FIG. 20, the third marker element 308 can be a wire 310. The wire 310 can have a twisted configuration having a plurality of loops 312. In an embodiment, the wire 310 of the biopsy site marker 300 can be braided with the second marker element 306. As seen in FIG. 21, the third marker element 308 can be a cylinder 314. In a further embodiment, the third marker element 308 may be a polymeric coating.

In an embodiment, the third marker element 308 can be imaged by a modality that is different than the imaging modality of the first marker element 302 and different than the imaging modality of the second marker element 306 of the biopsy site marker 300. For instance, the material of the third marker element 308 is different than the material of the first marker element 302 and the second marker element 306, so the first marker element 302, second marker element 306, and third marker element 308 can be imaged by three different imaging modalities. For instance, the first marker element 302 is a polymer, the second marker element 306 is a shape-memory material, and the third marker element 308 is another polymer. As stated earlier, imaging modalities include radiographic imaging modalities, magnetic resonance imaging (MRI), ultrasonography, fluoroscopy, or computed tomography.

In a further embodiment, the biopsy site marker 300 may further include a bioabsorbable cover. In an embodiment, the bioabsorbable cover is any suitable material used to encapsulate a medical implant that biodegrades within the biopsy cavity without any adverse reactions to the patient. Bioabsorbable materials include, for example, aliphatic polyesters such as homopolymers and copolymers of lactic acid, glycolic acid, lactide, glycolide, para-dioxanone, trimethylene carbonate, ε-caprolactone, polyorthoesters, polyethylene oxide, and blends thereof.

Figure 22:
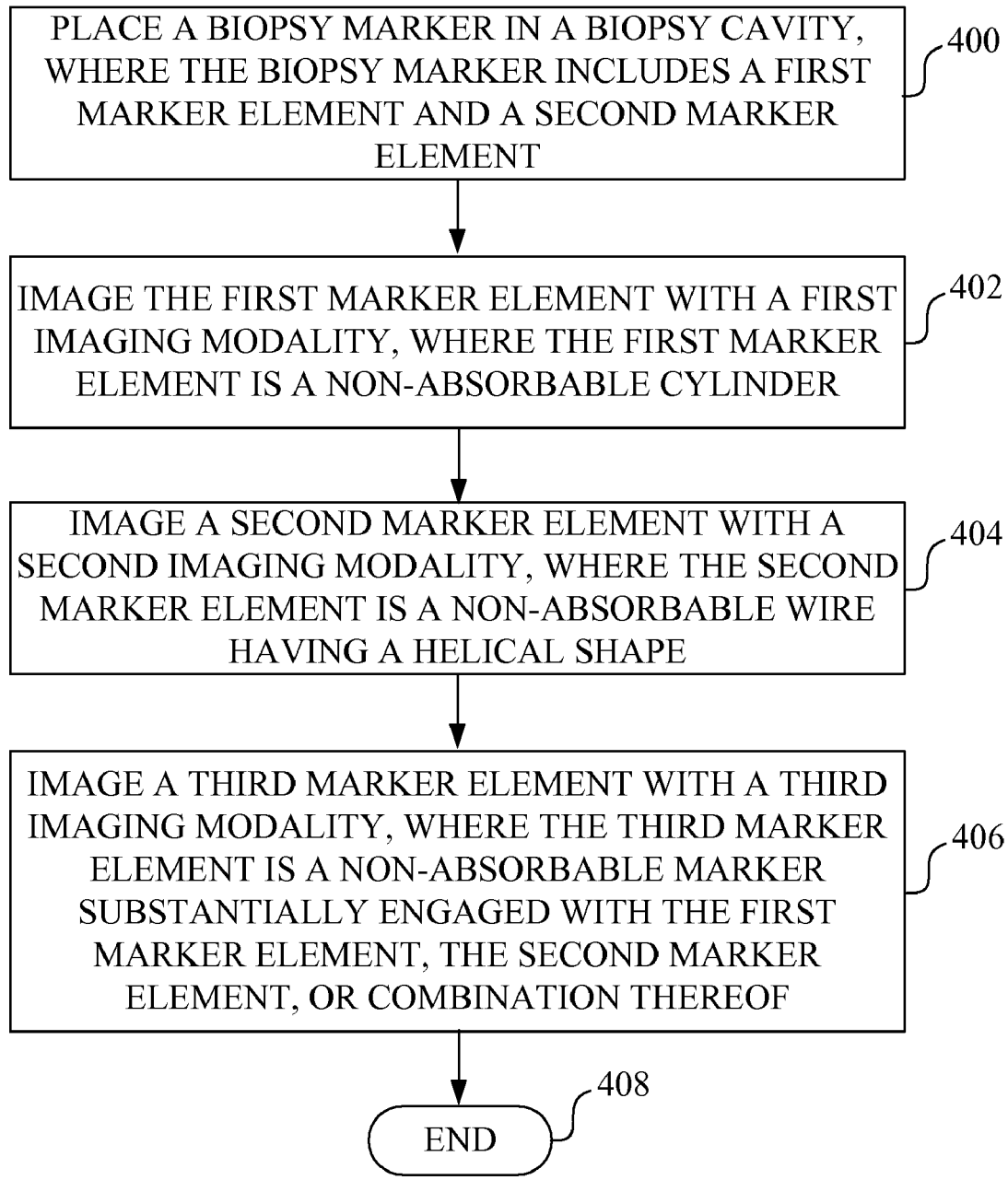
FIG. 22 is a flow chart illustrating an exemplary first method of imaging a subcutaneous biopsy cavity.

Referring now to FIG. 22, a method of imaging a subcutaneous biopsy cavity is shown and commences at block 400. At block 400, a biopsy marker is placed into a biopsy cavity. The biopsy marker includes a first marker element and a second marker element. In an embodiment, the first marker element is a non-absorbable cylinder. The second marker element is a non-absorbable wire having a helical shape. In an exemplary embodiment, the non-absorbable wire is substantially engaged with the first marker element.

At block 402, the first marker element is detected using a first imaging modality. Medical imaging modalities include, for example, radiographic imaging modalities, magnetic resonance imaging (MRI), ultrasonography, fluoroscopy, or computed tomography.

At block 404, the biopsy marker element may be detected using a second imaging modality. The second imaging modality may be any of the medical imaging modalities described above. In a further embodiment, the second imaging modality is different than the first imaging modality.

At block 406, the biopsy marker element may be detected using a third imaging modality. For instance, the biopsy marker can include a third marker element that is a non-absorbable material and substantially engaged with the first marker element, the second marker element, or a combination thereof. The third marker element can be in any suitable configuration such that it is substantially engaged with the first marker element, the second marker element, or combination thereof. In an embodiment, the third marker element is a wire. In an embodiment, the third marker element has a twisted configuration with a plurality of loops. In an embodiment, the second marker element and the third marker element may be braided. In an embodiment, the third marker element is a polymer coating. The third imaging modality may be any of the medical imaging modalities described above. In a further embodiment, the third imaging modality is different than the first imaging modality and the second imaging modality. The method can end at state 408.

Figure 23:
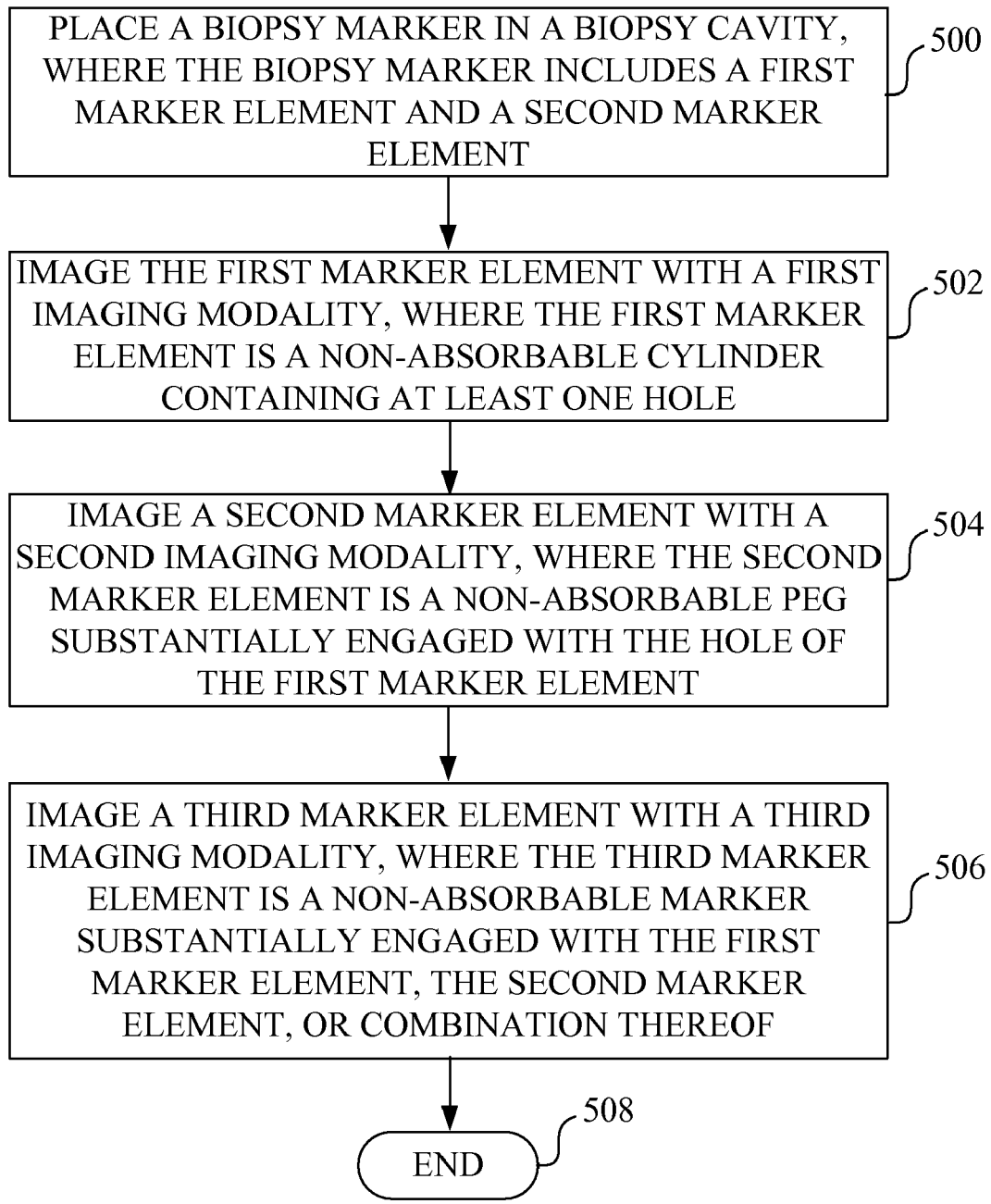
FIG. 23 is a flow chart illustrating an exemplary second method of imaging a subcutaneous biopsy cavity.

Referring now to FIG. 23, a method of imaging a subcutaneous biopsy cavity is shown and commences at block 500. At block 500, a biopsy marker is placed into a biopsy cavity. The biopsy marker includes a first marker element and a second marker element. In an embodiment, the first marker element is a non-absorbable cylinder having at least one hole. The second marker element is a non-absorbable peg substantially engaged with the hole of the first marker element.

At block 502, the first marker element is detected using a first imaging modality. Medical imaging modalities include, for example, radiographic imaging modalities, magnetic resonance imaging (MRI), ultrasonography, fluoroscopy, or computed tomography.

At block 504, the second marker element may be detected using a second imaging modality. The second imaging modality may be any of the medical imaging modalities described above. In a further embodiment, the second imaging modality is different than the first imaging modality.

At block 506, the biopsy marker element may be detected using a third imaging modality. The third imaging modality may be any of the medical imaging modalities described above. In a further embodiment, the third imaging modality is different than the first imaging modality and the second imaging modality. For instance, the biopsy marker can include a third marker element that is a non-absorbable material and substantially engaged with the first marker element, the second marker element, or combination thereof. In an embodiment, the third marker element is a coating. In an embodiment, the third marker element is a wire. The third marker element may have a twisted configuration having a plurality of loops. In an embodiment, the first marker element may include a second hold and the third marker element may be a peg substantially engaged with the second hole. The method can end at state 508.

Figure 24:
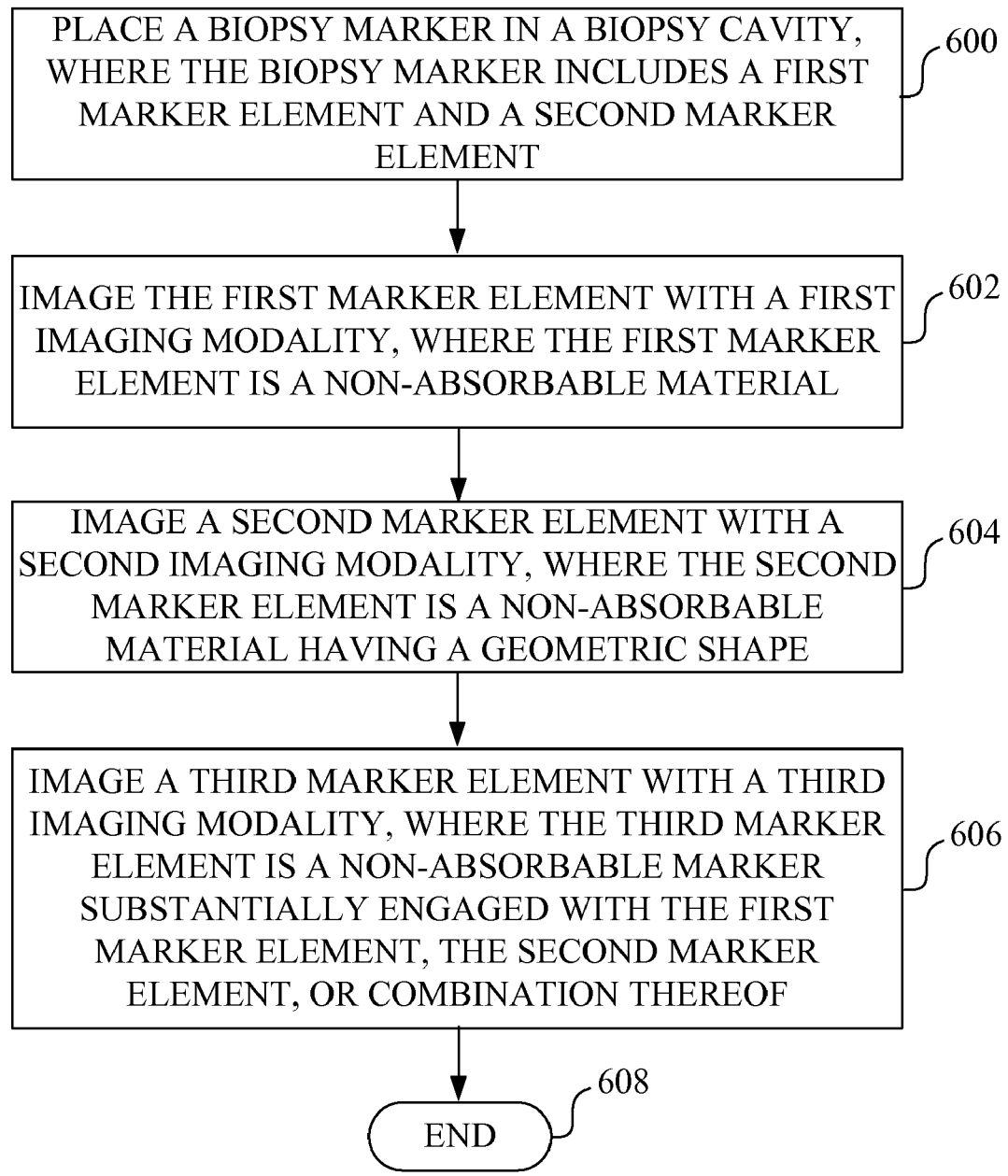
FIG. 24 is a flow chart illustrating an exemplary third method of imaging a subcutaneous biopsy cavity.

Referring now to FIG. 24, a method of imaging a subcutaneous biopsy cavity is shown and commences at block 600. At block 600, a biopsy marker is placed into a biopsy cavity. The biopsy marker includes a first marker element and a second marker element. In an embodiment, the first marker element is a non-absorbable material. In an exemplary embodiment, the first marker element is a cylinder. The second marker element is a non-absorbable material substantially engaged with the first marker element. The second marker element can be in any suitable configuration such that it is substantially engaged with the first marker element. In an exemplary embodiment, the second marker element has a geometric shape to increase its echogenity. In an embodiment, the second marker element has a shape such as a mesh shape, a pyramid shape, a cube shape, a sphere shape, a rectangular shape, or a square shape.

At block 602, the first marker element is detected using a first imaging modality. Medical imaging modalities include, for example, radiographic imaging modalities, magnetic resonance imaging (MRI), ultrasonography, fluoroscopy, or computed tomography.

At block 604, the second biopsy marker element may be detected using a second imaging modality. The second imaging modality may be any of the medical imaging modalities described above. In a further embodiment, the second imaging modality is different than the first imaging modality.

At block 606, the biopsy marker element may be detected using a third imaging modality. For instance, the biopsy marker can include a third marker element that is a non-absorbable material and substantially engaged with the first marker element, the second marker element, or combination thereof. The third marker element can be in any suitable configuration such that it is substantially engaged with the first marker element, the second marker element, or combination thereof. In an embodiment, the third marker element is a polymer coating. In an embodiment, the third marker element is a wire. In an embodiment, the third marker element has a twisted configuration with a plurality of loops. In an embodiment, the second marker element and the third marker element may be braided. In an embodiment, the third marker element is a cylinder. The third imaging modality may be any of the medical imaging modalities described above. In a further embodiment, the third imaging modality is different than the first imaging modality and the second imaging modality. The method can end at state 608.

The embodiments described herein provide one or more biopsy site markers that are configured to maximize echogenity during medical imaging. Further, the marking devices are configured such that the markers may be imaged by multiple modalities to decrease any trauma to the patient. The biopsy site markers described herein can provide imaging for multiple modalities unlike common biopsy site markers. Moreover, the materials and configurations of the marker elements can be chosen to fill biopsy voids as well as to prevent migration from the biopsy site.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A biopsy site marker comprising:
a first marker element configured for detection by a first imaging modality, wherein the first marker element is a non-absorbable cylinder;
a second marker element configured for detection by a second imaging modality different from the first imaging modality, wherein the second marker element is a non-absorbable wire having a first helical shape positioned around a longitudinal extent of the non-absorbable cylinder of the first marker element; and
a third marker element having a second helical shape overlapped with the first helical shape and positioned around a longitudinal extent of the non-absorbable cylinder of the first marker element.

2. The marker of claim 1, wherein the first marker element is a polymer.

3. The marker of claim 1, wherein the first marker element is formed entirely from non-magnetic material.

4. The marker of claim 1, wherein the non-absorbable wire has a twisted configuration.

5. The marker of claim 1, wherein the second marker element is a shape-memory material.

6. The marker of claim 1, wherein the third non-absorbable marker element is detectable by a third imaging modality and not detectable by the first imaging modality and not detectable by the second imaging modality.

7. The marker of claim 6, wherein the third marker element is substantially engaged with each of the first marker element and the second marker element.

8. The marker of claim 1, wherein the third marker element is a third marker wire.

9. The marker of claim 8, wherein the third marker wire is substantially engaged with the non-absorbable wire.

10. The marker of claim 8, wherein the third marker wire has a twisted configuration.

11. The marker of claim 8, wherein the non-absorbable wire and third marker wire are braided.

12. The marker of claim 7, wherein the third marker element is a polymer coating.

13. The marker of claim 6, wherein the third imaging modality is one of ultrasonography, fluoroscopy, magnetic resonance imaging, X-ray, and computed tomography.

14. The marker of claim 1, wherein the first imaging modality is one of ultrasonography, fluoroscopy, magnetic resonance imaging, X-ray, and computed tomography.

15. The marker of claim 1, wherein the second imaging modality is one of ultrasonography, fluoroscopy, magnetic resonance imaging, X-ray, and computed tomography.

16. The marker of claim 1, further comprising a bioabsorbable cover.

17. A biopsy site marker comprising:
a first marker element configured for detection by a first imaging modality, wherein the first marker element is a non-absorbable cylinder having a cylindrical side surface having at least one hole; and
a second marker element configured for detection by a second imaging modality different from the first imaging modality, wherein the second marker element is a non-absorbable peg substantially engaged with the hole of the first marker element, the non-absorbable peg being configured to extend distally outwardly from the hole away from the cylindrical side surface of the first marker element.

18. The marker of claim 17, wherein the first marker element is a polymer.

19. The marker of claim 17, wherein the first marker element is formed entirely from non-magnetic material.

20. The marker of claim 17, further comprising a third non-absorbable marker element substantially engaged with at least one on the first marker element and the second marker element.

21. The marker of claim 20, wherein the third marker element is detectable by a third imaging modality and not detectable by the first imaging modality and not detectable by the second imaging modality.

22. The marker of claim 20, wherein the third marker element is a polymer coating.

23. The marker of claim 20, wherein the third marker element is a wire.

24. The marker of claim 23, wherein the wire has a twisted configuration.

25. The marker of claim 17, comprising a second hole in the cylindrical side surface of the first marker element and a third marker element formed as a second non-absorbable peg substantially engaged with the second hole, the second non-absorbable peg being configured to extend distally outwardly from the second hole away from the cylindrical side surface of the first marker element.

26. The marker of claim 17, wherein the first imaging modality is one of ultrasonography, fluoroscopy, magnetic resonance imaging, X-ray, and computed tomography.

27. The marker of claim 17, wherein the second imaging modality is one of ultrasonography, fluoroscopy, magnetic resonance imaging, X-ray, and computed tomography.

28. The marker of claim 20, wherein the third imaging modality is one of ultrasonography, fluoroscopy, magnetic resonance imaging, X-ray, and computed tomography.

29. The marker of claim 17, further comprising a bioabsorbable cover.

30. A biopsy site marker comprising:
a first marker element, wherein the first marker element is a non-absorbable material configured for detection by a first imaging modality; and
a second marker element configured for detection by a second imaging modality different from the first imaging modality, wherein the second marker element is a non-absorbable material, and wherein the second marker is a wire having bends to form a predetermined closed geometric shape having a plurality of side segments, and with the first marker element being engaged with one of the side segments.

31. The marker of claim 30, wherein the first marker element is a polymer.

32. The marker of claim 30, wherein the first marker element is formed from at least one of a metal and a metal alloy.

33. The marker of claim 30, wherein the first marker element is a cylinder.

34. The marker of claim 30, wherein the first marker element is a wire.

35. The marker of claim 30, wherein the second marker element is a polymer material.

36. The marker of claim 30, wherein the second marker element is a shape-memory material.

37. The marker of claim 30, wherein the second marker element has one of a pyramid shape, a cube shape, a sphere shape, a rectangular shape, and a square shape.

38. The marker of claim 30, wherein the wire has a twisted configuration.

39. The marker of claim 30, further comprising a third non-absorbable marker element engaged with at least one of the first marker element and the second marker element detectable by a third imaging modality different from the first imaging modality and different from the second imaging modality.

40. The marker of claim 39, wherein the third marker element is substantially engaged with both of the first marker element and the second marker element.

41. The marker of claim 39, wherein the third marker element is a polymer coating.

42. The marker of claim 39, wherein the third marker element is a third marker wire.

43. The marker of claim 42, wherein the third marker wire has a twisted configuration.

44. The marker of claim 42, wherein the third marker element and the second marker element are braided.

45. The marker of claim 39, wherein the third marker element is a cylinder and the third marker element is engaged with one of the side segments of the second marker element different from the side segment engaged by the first marker element.

46. The marker of claim 30, wherein the first imaging modality is one of ultrasonography, fluoroscopy, magnetic resonance imaging, X-ray, and computed tomography.

47. The marker of claim 30, wherein the second imaging modality is one of ultrasonography, fluoroscopy, magnetic resonance imaging, X-ray, and computed tomography.

48. The marker of claim 39, wherein the third imaging modality is one of ultrasonography, fluoroscopy, magnetic resonance imaging, X-ray, and computed tomography.

49. The marker of claim 30, further comprising a bioabsorbable cover that encapsulates the marker.

50. A method for imaging a subcutaneous biopsy cavity comprising:
   placing a marker element into the biopsy cavity, wherein the marker element includes
      a first marker element, wherein the first marker element is a non-absorbable cylinder;
      a second marker element, wherein the second marker element is a non-absorbable wire having a first helical shape positioned around a longitudinal extent of the non-absorbable cylinder of the first marker element; and
      a third marker element having a second helical shape overlapped with the first helical shape and positioned around a longitudinal extent of the non-absorbable cylinder of the first marker element;
   detecting the first marker element using a first imaging modality; and
   detecting the second marker element using a second imaging modality.

51. The method of claim 50, wherein the first imaging modality is one of ultrasonography, fluoroscopy, magnetic resonance imaging, X-ray, and computed tomography.

52. The method of claim 51, wherein the second imaging modality is a different one of ultrasonography, fluoroscopy, magnetic resonance imaging, X-ray, and computed tomography.

53. The method of claim 50, wherein the third non-absorbable marker element is substantially engaged with at least one of the first marker element and the second marker element.

54. The method of claim 53, further comprising detecting the third marker element using a third imaging modality, wherein the third imaging modality is different than the first imaging modality and the second imaging modality.

55. The method of claim 54, wherein the third imaging modality is one of ultrasonography, fluoroscopy, magnetic resonance imaging, X-ray, and computed tomography.

56. A method for imaging a subcutaneous biopsy cavity comprising:
   placing a marker element into the biopsy cavity, wherein the marker element includes
      a first marker element, wherein the first marker element includes a non-absorbable cylinder having a cylindrical side surface containing at least one hole, and
      a second marker element, wherein the second marker element is a non-absorbable peg substantially engaged with the hole of the first marker element and which extends distally outwardly from the hole away from the cylindrical side surface of the first marker element;
   detecting the first marker element using a first imaging modality; and
   detecting the second marker element using a second imaging modality.

57. The method of claim 56, wherein the first imaging modality is one of ultrasonography, fluoroscopy, magnetic resonance imaging, X-ray, and computed tomography.

58. The method of claim 57, wherein the second imaging modality is a different one of ultrasonography, fluoroscopy, magnetic resonance imaging, X-ray, and computed tomography.

59. The method of claim 56, wherein the marker element further includes a third non-absorbable marker element substantially engaged with at least one of the first marker element and the second marker element.

60. The method of claim 59, further comprising detecting the third marker element using a third imaging modality, wherein the third imaging modality is different than the first imaging modality and the second imaging modality.

61. The method of claim 60, wherein the third imaging modality is one of ultrasonography, fluoroscopy, magnetic resonance imaging, X-ray, and computed tomography.

62. A method for imaging a subcutaneous biopsy cavity comprising:
   placing a marker element into the biopsy cavity, wherein the marker element includes
      a first marker element, wherein the first marker element includes a non-absorbable material, and
      a second marker element, wherein the second marker element is a non-absorbable material substantially engaged with the first marker element, the second marker element being a wire having bends to form a predetermined closed geometric shape having a plurality of side segments, and with the first marker element being engaged with one of the side segments;
   detecting the first marker element using a first imaging modality; and
   detecting the second marker element using a second imaging modality.

63. The method of claim 62, wherein the first imaging modality is one of ultrasonography, fluoroscopy, magnetic resonance imaging, X-ray, and computed tomography.

64. The method of claim 62, wherein the second imaging modality is one of ultrasonography, fluoroscopy, magnetic resonance imaging, X-ray, and computed tomography.

65. The method of claim 62, wherein the marker element further includes a third non-absorbable marker element engaged with one of the side segments of the second marker element different from the side segment engaged by the first marker element.

66. The method of claim 65, further comprising detecting the third marker element using a third imaging modality, wherein the third imaging modality is different than the first imaging modality and the second imaging modality.

67. The method of claim 66, wherein the third imaging modality is one of ultrasonography, fluoroscopy, magnetic resonance imaging, X-ray, or computed tomography.

68. The method of claim 66, wherein the predetermined shape is one of a pyramid shape, a polygonal shape, and a sphere shape.

* * * * *